United States Patent [19]

Venin et al.

[11] 4,360,026
[45] Nov. 23, 1982

[54] DEFIBRILLATOR

[76] Inventors: Igor V. Venin, ulitsa Pozharskogo, 2, kv. 9; Oleg L. Gonopolsky, ulitsa Dovbusha, 11, kv. 5; Valery P. Zhuk, ulitsa Ulyanovskaya, 5, kv. 9; Vladimir I. Rodionov, ulitsa Zayachkovskogo, 7, kv. 27; Andrei A. Smerdov, ulitsa Stepana Tudora, 16, kv. 5; Alexandr G. Tischenko, ulitsa Nechuya-Levitskogo, 15, kv. 5, all of Lvov, U.S.S.R.

[21] Appl. No.: 215,519

[22] Filed: Dec. 11, 1980

[30] Foreign Application Priority Data

Feb. 28, 1980 [SU] U.S.S.R. ................................ 2882806

[51] Int. Cl.³ ............................................. A61N 1/36
[52] U.S. Cl. ................................. 128/419 D; 128/1 C
[58] Field of Search ........... 128/419 D, 419 R, 419 S, 128/1 C

[56] References Cited

U.S. PATENT DOCUMENTS 3,320,947  5/1967  Knoll .............................. 128/419 R
3,653,387  4/1972  Ceier .............................. 128/419 D

*Primary Examiner*—William E. Kamm
*Attorney, Agent, or Firm*—Fleit & Jacobson

[57] ABSTRACT

A defibrillator comprises a discharging circuit provided with a storage capacitor, a controlled contactor, and electrodes for defibrillation connected in series therebetween. The output of a voltage source and a control unit for adjusting and controlling a voltage across the capacitor are connected to the capacitor. The voltage source input is connected to the output of the control unit. The defibrillator comprises two AND gates, each having two inputs and an output, a unit for starting defibrillation, and an electronarcosis device. The first AND gate has an input connected to the output of the control unit. The first AND gate has a second input connected to the unit for starting defibrillation, while the first AND gate output is connected to the first input of the second AND gate. The second AND gate output is connected to the controlled contactor input. The electronarcosis device comprises a shaping unit for shaping and starting a narcotizing current having an input and two outputs, a signal shaper for starting defibrillation, and electrodes for narcosis. The shaping unit input, is connected to first AND gate output, while the first output is connected to the signal shaper input and the second output is connected to the electrodes for narcosis. The signal shaper output is connected to the second input of the second AND gate.

1 Claim, 1 Drawing Figure

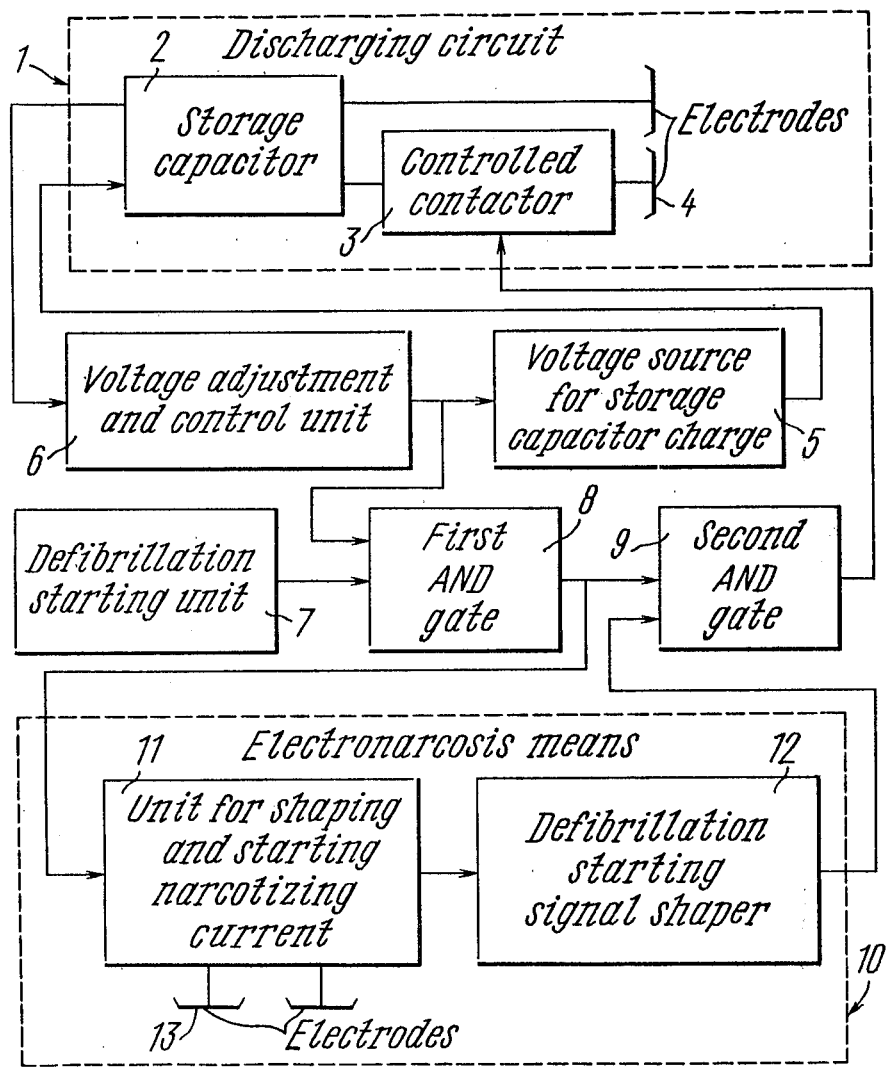

DEFIBRILLATOR

BACKGROUND OF THE INVENTION

1. Field of the Invention

The invention relates to the medical instrument engineering, and namely to the instruments for stopping heart fibrillation by applying short-time electric pulses, i.e. to defibrillators.

The invention may prove most advantageous in medicine for treatment during acute and chronic rhytm disturbances, particularly during resuscitation.

Due to the fact that defibrillation of the heart is accompanied by excessive painful sensations which can lead to the pain shock, it is necessary to apply a short-time narcosis during treatment. It is most expedient to use a short-time electronarcosis caused by interference currents, said electronarcosis being characterized by the absence of side and toxic effects on the patient's organism, which effects are especially dangerous in predeterminal and terminal states.

Instruments intended for heart defibrillation are known for a comparatively long time, however up to now prior art defibrillators cannot provide in the process of operation an automatically strict sequence of effects of a narcotizing and defibrillating current on a patient which fact, during emergency medical treatment of a patient being in a grave condition, may lead to operator's mistakes thus decreasing safety of the treatment procedure.

2. Description of the Prior Art

Known in the art are defibrillators (British Pat. No. 1,481,469, I. V. Venin et al., DI-03 and DKI-01 defibrillators, "Novosti meditsinskogo priborostroenia", VNIIMP, Moscow, 1973, pp. 48–53), comprising a discharging circuit provided with a storage capacitor, a controlled contactor, and electrodes, being connected in series therebetween. The storage capacitor is connected to a voltage source for charging said storage capacitor, and to the input of a unit for adjusting and controlling a voltage across the storage capacitor. The output of said unit for controlling the voltage is connected to the input of the voltage source. A unit for starting defibrillation is connected to the input of the controlled contactor.

The unit for adjusting and controlling the voltage is constructed as a kilovoltmeter and a pushbutton for switching on the voltage source.

Prior to starting the defibrillation procedure, electrodes of an electronarcosis apparatus are fixed on the patient's head, while electrodes of the defibrillator are fixed on the chest. Then an operator depresses the pushbutton of the unit for adjusting and controlling the voltage, and holding the pushbutton in the depressed position, carries out controlled charging the storage capacitor. Following this, the operator actuates the electronarcosis apparatus and without interrupting the effect of the narcotizing current on the patient, switches on the unit for starting defibrillation. In doing so, there occurs starting the controlled contactor, and a pulse of the defibrillator is fed to the patient's chest. Then the operator disconnects the electronarcosis apparatus.

With such a procedure, the time of effect of electronarcosis prior to and after the effect of the defibrillating current is determined by the operator. This can lead to operator's mistakes, especially under strenous conditions of emergency treatment of a patient being in a grave condition, which mistakes worsen the patient's state. For example, the duration of electronarcosis may be excessively decreased thus resulting in the fact that defibrillation will occur prior to the beginning of the narcotizing effect of the current. Moreover, due to a mistake, defibrillation may also take place after the narcotizing effect of the current is over.

Said disadvantages are to a certain degree eliminated by a defibrillator (I. V. Venin et al., Di-03 and DKI-01 defibrillators, "Novosti meditsinskogo priborostrojenija", VNIIMP, Moscow, 1973, pp. 48–53) comprising a discharging circuit provided with a storage capacitor, a controlled contactor, and electrodes, being connected in series therebetween. The storage capacitor is connected to a voltage source for charging said storage capacitor, and to the input of a unit for adjusting and controlling a voltage across the storage capacitor.

The output of said unit for adjusting and controlling the voltage is connected to the input of the voltage source. The defibrillator further comprises an AND gate having two inputs and an output, and a unit for starting defibrillation. The first input of the AND gate is connected to the output of the unit for starting defibrillation, while the second input of said AND gate is a synchronizing input of the defibrillator to synchronize the effects of the defibrillating current and of an external source of a signal, and the output of the AND gate is connected to the input of the controlled contactor.

Prior to starting the defibrillation procedure, an operator connects the synchronizing input of the defibrillator (the second input of the AND gate) to an electronarcosis apparatus following which electrodes of the electronarcosis apparatus are fixed on the patient's head, while electrodes of the defibrillator are fixed on the chest. Then the storage capacitor is charged up to a voltage necessary to carry out defibrillation, said voltage being automatically maintained at a predetermined level. The operator actuates the unit for starting defibrillation and then switches on the electronarcosis apparatus. As the patient is under the effect of the narcotizing current a signal is fed from the electronarcosis apparatus to the synchronizing input of the defibrillator (the second input of the AND gate). In doing so, at the output of the AND gate there appears a pulse which is fed to the contrlled contactor thereby actuating said contactor, and a pulse of the defibrillator is fed to the patient's chest against the background of the narcotizing effect.

However, in the process of operation of the above defibrillator, especially under conditions of treating patients being in the terminal state, there exists the danger of synchronous effect of electronarcosis and the defibrillating current on the patient when the operator switches on the unit for starting defibrillation while the voltage across the storage capacitor has not yet reached, in the process of charging said capacitor, the level required for defibrillation.

It is known that discharging the storage capacitor under a voltage being lower than that required for defibrillation, while coinciding with the vulnerable phase of the cardiac cycle, may cause heat fibrillation.

Said disadvantage is eliminated by the Defiscop defibrillator manufactured by the "Thomson" company (France), which defibrillator comprises a discharging circuit provided with a storage capacitor, a controlled contactor, and electrodes for defibrillation, being connected in series therebetween. The storage capacitor is connected to the output of a voltage source to charge said storage capacitor, and to the input of a unit for adjusting and controlling a voltage across the storage capacitor. The input of the voltage source is connected to the output of the unit for adjusting and controlling the voltage. The defibrillator further comprises a unit for starting the defibrillator, and two AND gate, each of said gates having two inputs and an output. The first input of the first AND gate is connected to the output of the unit for adjusting and controlling the voltage. The second input of the first AND gate is connected to the unit for starting defibrillation. The output of the first AND gate is connected to the first input of the second AND gate whose second input is a synchronizing input of the defibrillator. The output of said second AND gate is connected to the input of the controlled contactor.

Prior to starting the defibrillation procedure, the operator connects the synchronizing input of the defibrillator (the second input of the second AND gate) to an electronarcosis apparatus following which electrodes of the electronarcosis apparatus are fixed on the patient's head, while electrodes of the defibrillator are fixed on the chest. Then the storage capacitor is charged up to a voltage required for defibrillation. The magnitude of this voltage is then automatically maintained at a predetermined level. Following this, the operator actuates the unit for starting defibrillation and then switches on the electronarcosis apparatus. As the patient is under the effect of the narcotizing current, a signal is fed from the electronarcosis apparatus to the synchronizing input of the defibrillator (the second input of the second AND gate). A signal from the unit for starting defibrillation is fed to the first input of said second AND gate. It is understood that this signal may be fed only in the case when at the output of the unit for adjusting and controlling the voltage there exists a signal indicating that the level of the voltage across the storage capacitor required for defibrillation is reached. Thus, the effect on the patient of the defibrillating current being of a lower magnitude than required is eliminated in this defibrillator. After both signals have been fed to the inputs of the second AND gate, a pulse appears at the output thereof, said pulse being fed to the input of the controlled contactor. In doing so, said contactor gets actuated, and a pulse of the defibrillator is fed to the patient's chest against the background of the narcotizing effect.

However, in the process of operation of the above defibrillator, especially under conditions of treating patients being in the terminal state, there exists the danger of the effect of only the narcotizing current on the patient without subsequent defibrillation. This becomes possible due to the fact that using the above defibrillator, the operator accomplishes defibrillation being synchronous with electronarcosis by carrying out two subsequent actions: actuation of the unit for starting defibrillation and switching on the electronarcosis apparatus.

While the effect of the defibrillating current on the patient is possible only in the case when the defibrillator is completely ready for operation, the effect of the narcotizing current is also possible when the defibrillator is not ready for operation. Thus, the gravity of the situation when carrying out emergency treatment of the patient being in a critical state, may promote operator's mistakes, and utilization of the above described defibrillator may lead to unwarranted effects of the narcotizing current on the patient thereby decreasing safety of the treatment procedure.

Moreover, in operation of the above described defibrillator the operator has to spend some time for connecting the narcosis apparatus thereto, and to be especially careful to see which apparatus and in which sequence is to be put in operation. Under conditions of a strenous situation the above consideration results in a considerable complication of apparatus maintenance thereby leading to certain losses of time which time is so valuable during this period.

SUMMARY OF THE INVENTION

The main object of the present invention is to provide a defibrillator the circuit arrangement of which would provide in the process of operation thereof an automatically strict sequence of effects of the narcotizing and the defibrillating current on the patient.

Another object of the invention is to simplify maintenance of the defibrillator.

Still another object of the invention is to decrease time expenditure required for auxiliary operations.

These and other objects of the present invention are attained by that a defibrillator comprising a discharging circuit provided with a storage capacitor, a controlled contactor, and electrodes for defibrillation being connected in series therebetween, a voltage source for charging the storage capacitor having an input and an output which output being connected to said storage capacitor, a unit for adjusting and controlling a voltage across the storage capacitor, said unit having an input connected to said storage capacitor and an output connected to the input of the voltage source, a unit for starting defibrillation, and two AND gates, each of said gates having two inputs and an output, the first input of the first AND gate being connected to the output of the unit for adjusting and controlling the voltage, while the second input of said first AND gate is connected to the unit for starting defibrillation, and the output of said first AND gate being connected to the first input of the second AND gate whose output is in turn connected to the input of the controlled contactor, according to the invention, is provided with electronarcosis means comprising a unit for shaping and starting a narcotizing current having an input and two outputs, and a shaper of a signal for starting defibrillation, the input of the unit for shaping and starting the narcotizing current being connected to the output of the first AND gate, the first output of said unit for shaping and starting the narcotizing current being connected to the input of the shaper of a signal for starting defibrillation whose output is in turn connected to the second input of the second AND gate, while the second output of the unit for shaping and starting the narcotizing current is connected to electrodes for narcosis.

Incorporating electronarcosis means into the circuitry of the defibrillator, said means having a unit for shaping and starting the narcotizing current and being connected with the input thereof to the output of the first AND gate, one of the inputs of said gate being connected to the output of the unit for adjusting and controlling the voltage across the storage capacitor, makes it possible to provide the effect of the narcotizing current on the patient only in the case when the level of the voltage across the storage capacitor corresponds to that required for defibrillation. The presence of the shaper for a signal for starting defibrillation within said electronarcosis means, the input of said shaper being connected to one of the outputs of the unit for shaping and starting the narcotizing current, while the output thereof is connected to one of the inputs of the second AND gate, provides for starting the defibrillating effect following the effect of the narcotizing current on the patient (after a predetermined time delay). Thus, the above described defibrillator ensures during the treatment procedure an automatically strict sequence of effects of the narcotizing and the defibrillating current on the patient. This fact eliminates the possibility of operator's mistakes in the course of emergency treatment of the patient being in a critical state thereby increasing safety of the treatment procedure.

The above consideration is also promoted by a considerable simplification of maintenance of the claimed defibrillator, and by minimum expenditure of the time required to put said defibrillator into operation.

It is sufficient for the operator maintaining the inventive defibrillator to accomplish only one action, i.e. to switch on the unit for starting defibrillation.

BRIEF DESCRIPTION OF DRAWINGS

The present invention is further explained in terms of specific embodiments thereof with reference to the accompanying drawing which shows the block diagram of the defibrillator of the invention.

DESCRIPTION OF THE PREFERRED EMBODIMENT

The defibrillator comprises a discharging circuit 1 provided with a storage capacitor 2, a controlled contactor 3, and electrodes 4 for defibrillation, being connected in series therebetween. The storage capacitor 2 is connected to the output of a voltage source 5 for charging said storage capacitor 2. The input of the voltage source 5 is connected to the output of a unit 6 for adjusting and controlling the voltage across the storage capacitor 2. The input of said unit 6 for adjusting and controlling the voltage is connected to the storage capacitor 2.

The defibrillator further comprises a unit 7 for starting defibrillation and two AND gates 8 and 9. Each of said elements 8 and 9 is provided with two inputs and one output. The first input of the first element 8 is connected to the output of the unit 6 for adjusting and controlling the voltage. The second output of the first AND gate 8 is connected to the unit 7 for starting defibrillation. The output of the first AND gate 8 is connected to a second input of the second AND gate 9, while the output of said second AND gate 9 is connected to the input of the controlled contactor 3.

According to the invention, the defibrillator is provided with electronarcosis means 10 comprising a unit 11 for shaping and starting the narcotizing current, a shaper 12 of a signal for starting defibrillation, and electrodes 13 for narcosis. The unit 11 for shaping and starting the narcotizing current has an input connected to the output of the first AND gate 8, and two outputs. The first output of the unit 11 for shaping and starting the narcotizing current is connected to the input of the shaper 12 of a signal for starting defibrillation, while the second output thereof is connected to the electrodes 13 for narcosis. The output of the shaper 12 of a signal for starting defibrillation is connected to the second input of the second AND gate 9.

The above described defibrillator operates as follows.

Prior to the beginning of the defibrillation procedure, the operator fixes the electrodes 13 for narcosis on the patient's head, while electrodes 4 for defibrillation are fixed on the patient's chest. Then the operator switches on the voltage source 5 thereby starting the process of charging the storage capacitor 2 to a voltage required for defibrillation. The voltage of the charge across the storage capacitor 2 or a magnitude being proportional to said voltage is fed to the input of the unit 6 for adjusting and controlling the voltage. After the voltage across the storage capacitor 2 has reached the predetermined value, the signal being fed from the output of the unit 6 for adjusting and controlling the voltage to the input of the voltage source 5 disconnects the latter. The process of charging the storage capacitor 2 is stopped. At the same time, the signal from the output of the unit 6 for adjusting and controlling the voltage is fed to the first input of the first AND gate 8 thereby permitting the start of the defibrillator being ready to operation. Thus, the preparatory procedures are over.

The operator switches on the unit 7 for starting defibrillation, the signal from the output of said unit being fed to the second input of the first AND gate 8. With the signals being present at both inputs of the first AND gate 8, a signal is formed at the output of the latter, said signal being simultaneously fed to the first input of the second AND gate 9 and to the input of the unit 11 for shaping and starting the narcotizing current. At this moment the start-up of electronarcosis takes place, the narcotizing current is fed to the patient's head through the electrodes 13, and simultaneously a signal from the first output of the unit 11 for shaping and starting the narcotizing current is fed to the input of the shaper 12 of a signal for starting defibrillation. Following this, after a predetermined time interval from the moment of the beginning of electronarcosis, a signal for starting defibrillation is fed from the output of the shaper 12 of a signal for starting defibrillation to the second input of the second AND gate 9. With the presence of signals at both inputs of the second AND gate 9 which presence is possible only when electronarcosis means 10 is started and the discharging circuit 1 is prepared for operation (the voltage of a signal across the storage capacitor 2 has the magnitude necessary for defibrillation), the signal from the output of the second AND gate 9 is fed to the input of the controlled contactor 3 which contactor, while being actuated, closes the network of the discharging circuit 1, and a pulse of the defibrillator is fed to the patient's chest against the background of the narcotizing effect.

It is to be understood that the invention has been described herein in terms of a specific example of the embodiments thereof. Various modifications being apparent to those skilled in the art may be made in the invention without departing frop the spirit and scope thereof as defined in the claims.

What is claimed is:

1. A defibrillator comprising:
 a. a discharging circuit provided with
    a storage capacitor;
    a controlled contactor being connected in series to said storage capacitor;
    electrodes for defibrillation being connected in series to said storage capacitor and to said controlled contactor;
 b. a voltage source for charging said storage capacitor, said voltage source having an input, and an output which output being connected to said storage capacitor;
 c. a unit for adjusting and controlling a voltage across said storage capacitor, said unit having an input connected to said storage capacitor, and an output connected to the input of said voltage source;

d. a first AND gate having two inputs and an output, the first input being connected to the output of said unit for adjusting and controlling the voltage;

e. a second AND gate having two inputs and an output, the first input being connected to the output of said first AND gate, while the output thereof is connected to the input of said controlled contactor;

f. a unit for starting defibrillation, connected to the second input of said first AND gate;

g. electronarcosis means comprising:
   a unit for shaping and starting a narcotizing current having an input connected to the output of said first AND gate, and two outputs;
   a shaper of a signal for starting defibrillation having an input connected to the first output of said unit for shaping and starting the narcotizing current, and an output connected to the second input of said second AND gate;
   electrodes for narcosis being connected to the second output of said unit for shaping and starting the narcotizing current.

* * * * *